US007691602B1

(12) United States Patent
Hanson et al.

(10) Patent No.: US 7,691,602 B1
(45) Date of Patent: Apr. 6, 2010

(54) AGRICULTURAL SCREENING SYSTEM AND METHOD FOR DETECTION OF INFECTIOUS MICROORGANISMS

(75) Inventors: William P. Hanson, Carlisle, PA (US); Maureen A. Dyer, Mechanicsburg, PA (US); Robert E. Hetrick, Loysville, PA (US); Jennifer A. Oberholtzer, Mechanicsburg, PA (US); David E. Young, Pennsylvania Furnace, PA (US)

(73) Assignee: Hanson Technologies, Inc., Carlisle, PA (US)

( * ) Notice: Subject to any disclaimer, the term of this patent is extended or adjusted under 35 U.S.C. 154(b) by 161 days.

(21) Appl. No.: 12/041,630

(22) Filed: Mar. 3, 2008

Related U.S. Application Data

(60) Provisional application No. 60/913,903, filed on Apr. 25, 2007, provisional application No. 60/892,632, filed on Mar. 2, 2007.

(51) Int. Cl.
*C12Q 1/04* (2006.01)
(52) U.S. Cl. ...................................................... 435/34
(58) Field of Classification Search .................... 435/34
See application file for complete search history.

(56) References Cited

U.S. PATENT DOCUMENTS

| 3,486,298 | A | 12/1969 | Huebner |
| 4,385,113 | A | 5/1983 | Frosch |
| 5,024,762 | A | 6/1991 | Ford |
| 5,064,542 | A | 11/1991 | Negersmith |
| 5,200,065 | A | 4/1993 | Sinclair |
| 5,769,539 | A | 6/1998 | Tsang |
| 5,947,689 | A | 9/1999 | Schick |
| 6,139,727 | A | 10/2000 | Lockwood |
| 6,174,437 | B1 | 1/2001 | Haney |
| 6,306,350 | B1 | 10/2001 | Mereish |
| 6,949,355 | B2 | 9/2005 | Yamanishi |
| 7,179,372 | B2 | 2/2007 | Miller |
| 7,204,930 | B2 | 4/2007 | Nightingale |
| 2004/0000515 | A1 | 1/2004 | Harris |

FOREIGN PATENT DOCUMENTS

WO    WO2006096317    9/2006

OTHER PUBLICATIONS

Hill, V. et al., "Multistate Evaluation of an Ultrafiltration-Based Procedure for Simultaneous Recovery of Enteric Microbes in 100-Liter Tap Water Samples", Appl Environ Microbiol., 2007 73(13):4218-4225.
[No Authors Listed] "Protein Concentration and Diafiltration by Tangential Flow Filtration—an Overview", 2007 (15 pages).
Hastie, J. C. et al., "Concentrating Giardia cysts in water by tangential flow filtration compared with centrifugation", New Zealand Journal of Marine and Freshwater Research, 1992, 26:275-278.
Serra, C. et al., "Use of air sparging to improve backwash efficiency in hollow-fiber modules", Journal of Membrane Science, 1999, 161:95-113.

*Primary Examiner*—Tekchand Saidha
(74) *Attorney, Agent, or Firm*—Pepper Hamilton LLP

(57) ABSTRACT

The present invention is directed to methods and systems for rapidly identifying microorganisms such as bacteria, viruses, fungi and the like that may be present in an agricultural specimen. The methods of the present invention provide a process for rapidly and accurately identifying infectious or pathogenic microorganisms without the need for culturing. In addition, the methods of the present invention provide processes for assaying harvested agricultural crops for the presence of statistically significant quantities of microorganisms.

17 Claims, 4 Drawing Sheets

AGRICULTURAL SCREENING SYSTEM AND METHOD FOR DETECTION OF INFECTIOUS MICROORGANISMS

CROSS REFERENCE TO RELATED APPLICATIONS

This application claims priority to U.S. Provisional application No. 60/892,632, filed Mar. 2, 2007 and 60/913,903, filed Apr. 25, 2007 each of which is incorporated herein by reference.

FIELD OF THE INVENTION

The present invention is directed to systems and methods for testing for the presence of pathogenic microorganisms in vegetables, fruits, nuts and other plant material intended, e.g., for animal or human consumption.

BACKGROUND OF THE INVENTION

It is desirable to detect and quantify in foods and agricultural products analytes that may be indicative of the freshness or quality of the food. In routine quality control testing of foods, it is common practice to test for the presence of various contaminants, additives, degradation products, and chemical markers of microbial infestation, e.g., bacteria, bacterial endotoxins, mycotoxins, and the like. However, current methods by which such quality control testing is accomplished are typically either complex and skill-intensive analytical chemistry procedures or highly subjective and qualitative sensory evaluations, e.g., smell test, taste test, appearance, etc.

Furthermore, despite improvements in agriculture and food processing, outbreaks of disease from water-borne and food-borne pathogens still occur, including bacterial water- and food-borne diseases caused by *Clostridium botulinum* (botulism); *Clostridium perfringens* (food poisoning); *Staphylococcus aureus* (food poisoning); *Streptococcus* species (gastroenteritis); enteropathogenic *Escherichia coli* (gastroenteritis); *Shigella dysenteriae* (dysentery); *Salmonella* species (gastroenteritis); and *Vibrio cholerae* (cholera). There are also numerous water- and food-borne protozoan pathogens, such as *Entamoeba histolytica, Giardia lamblia, Cryptosporidium, Microsporidia,* and *Cyclospora*. In an attempt to avoid disease, food and water is often sampled and tested prior to distribution to determine whether it is contaminated by pathogenic microorganisms.

Numerous testing methods are available, but the following steps (or similar steps) are common to many methods: First, a pre-enrichment step is performed on a specimen to increase the number of pathogenic organisms present. The organisms are cultured in a non-selective growth medium typically for 24 hours or more. Pre-enrichment is usually necessary because pathogenic organisms may be present in very dilute amounts, thus making them difficult to detect. Second, an enrichment step may be performed in which a portion of the culture medium is transferred to an enrichment medium containing inhibitors that select for a pathogen of interest. The selected pathogen will grow further while other organisms are inhibited. Third, a measurement step is performed to discern whether pathogens of interest are present. Generally, a portion of the enrichment medium is streaked onto selective or differential agar media. The media will contain inhibitors effective against most organisms except the pathogen of interest. Indicator compounds (e.g. dyes) allow pathogen types to be visibly differentiated and thus indicate the presence and number of pathogens of interest. Exemplary alternative measurement steps are radioimmunoassay (RIA) tests, immunofluorescent assay (IFA) tests, enzyme immunoassay (EIA or ELISA) tests, DNA methods (e.g., PCR), and phage methods. Such methods are disadvantageous because they postpone distribution of fresh foodstuffs while specimens are culturing, particularly where freshness or spoilage concerns are present or it is otherwise impractical to store the food for extended periods. Furthermore, conventional methods typically only assay a small portion of an agricultural crop ($\leq 250$ g), which may lead to analytical results that are not representative of a harvested crop as a whole.

A need exists for a convenient rapid, cost-effective, and reliable method for testing for the presence of pathogens or infectious microorganisms in vegetables, fruits, nuts and other plant material intended, e.g., for animal or human consumption.

SUMMARY OF THE INVENTION

The present invention is directed to, among other things, methods and systems for rapidly identifying microorganisms such as bacteria, viruses, fungi and the like that may be present in an agricultural specimen. Methods of the present invention include processes for rapidly and accurately identifying infectious or pathogenic microorganisms without the need for culturing. In addition, the methods provide processes for assaying harvested agricultural crops for the presence of statistically significant quantities of microorganisms. In another embodiment, the present invention is also directed to methods of concentrating waterborne and food-borne microorganisms from fluids potentially contaminated by such microorganisms.

As used herein an agricultural specimen is any material to be assayed for the presence or concentration of a microorganism in an agricultural specimen or to make a qualitative assessment thereof. A specimen may be a fluid specimen that may be, e.g., water specimens, such as specimens of agricultural runoff water from oceans, seas, lakes, rivers, hydroponics, and the like; and food specimens, such as milk or wine or other beverages. Viscous liquid, semi-solid, or solid vegetation materials may be used to create liquid, eluates, suspensions, or extracts that can be specimens. Specimens may include a combination of liquids, solids, gasses, or any combination thereof, as, for example a suspension of cells of vegetable matter in a buffer or solution. Specimens may comprise biological materials, such as cells, microbes, organelles, and biochemical complexes. Liquid specimens may be made from solid, semisolid or highly viscous materials, such as soils, fecal matter, tissues, organs, biological fluids or other specimens that are not fluid in nature. For example, these solid or semi-solid specimens can be mixed with an appropriate solution, such as a buffer, such as a diluent or extraction buffer. The specimen may be macerated, frozen and thawed, or otherwise extracted to form a fluid.

In order to reliably and accurately detect pathogenic microorganisms without culturing an appropriate specimen size that statistically represents the source material should be chosen. For example, 20 kg would be an appropriate specimen size given a detection limit between 1,000 and 10,000 microorganisms; $2 \times 10^4$ provides enough pathogens for detection after processing with 50% efficiency at 10,000 and 25% at 5000. When a double stage filter step is employed, it should have high recovery rates so enough pathogens are moving to the next concentration step. A two-stage concentration process is desirable to achieve a 1000-fold concentration in a reasonable time period (e.g., a shorter time period than would be necessary if a specimen were cultured). Hollow tube and ceramic filtering may provide about 250 mL concentrate in about 20-40 minutes with a properly designed system. Where a smaller volume of concentrate is desired, the specimen may be concentrated again. Centrifuge and magnetic beads methods can both take volumes of 250 mL and concentrate it down to 1 mL in reasonable times (~15-30 min). The detection technology could include an array biosensor, PCR, rapid PCR, culturing, or any other method with limits of detection $\leq$10,000 organisms/mL. Using such a method, it is possible to detect pathogens without culturing saving significant amounts of time (1-3 hours versus 12-36 hours).

The invention provides an improvement over existing methods, which currently use specimen sizes of 100 g to about 250 g, by taking and using specimens from about 5 kg to about 50 kg (e.g., 20 kg), and then concentrating this large specimen into a small specimen size, followed by processing the specimen through a screening or testing system including an immunoassay, PCR method, or other biological testing method. For example, an array biosensor using a fluorescent sandwich assay can be used to screen the specimen for multiple pathogens or toxins, including doing the same test multiple times to reduce false positive and false negative rates.

An example embodiment of the invention includes the following process: Specimen preparation, which may include shredding the plant material, or simply washing the vegetable material without shredding, adding a solution such as phosphate buffered saline Tween® (TWEEN® is a registered trademark of ICI Americas, Inc. of Bridgewater, N.J.), or another detergent-containing solution that helps to remove or loosen the pathogens from the plant material, and agitating the solution to shake loose the pathogens. This may include ultrasonic agitation directly in the submerged solution, and/or mechanical agitation of the solution including a mixing process, which tends to agitate the plant material while spraying PBST on the plant material during spinning.

Multiple filtration steps follow specimen preparation, including rough filtering steps with one or multiple steps using 5 to 250 µm range filters, followed by a bacteria and virus capture nano-pore filter using, e.g., hollow fiber filter membranes, ceramic filters, or other filter media with 25-50 nm pores. The filters are run in the forward direction for a period of time passing large volumes of wash water from the prepare plant material through the filter, retaining the pathogens on the filter surface. The filters are then back flushed with pressures equal to or greater than the forward pressures, which dislodge the pathogens and other material clogged on the filter. This back flush is collected and provided to the next stage of concentration. The inventors have found that prior art methods of conducting such filtration and concentration steps are deficient because the back flush pressure is insufficient to recover the trapped microorganisms. Contrary to known techniques, the inventors have achieved superior results when the back flush pressure is higher than the pressure in the forward direction. In this manner, a significantly higher quantity of microorganisms may be collected and the lifetime of the filtration system is increased. The filters may be separated with valves and air bursts, or ultrasonic agitation may be used to dislodge material once it has clogged the filter and then removed through a valve as needed.

A second concentration step takes the concentrate from the nano-pore filters (with a typical volume of 10 mL to 5000 mL) and uses magnetic beads, centrifuge, nano-pore filtering, or electric field concentration to concentrate in a second stage with a back flush volume of about 0.1 to about 500 mL if using filters, or a separated volume of about 0.1 to about 500 mL if using centrifuge, magnetic beads, or electric fields to collect the pathogens in a smaller volume within the first stage concentrate, and the removing the unwanted material leaving a second concentrate ready for the pathogen detection systems. Electric field concentration uses positive and negative electrodes submerged in a tank. Pathogens are attracted to one of the electrodes, and concentrations of 100-fold or more may be achieved by collecting pathogens near the electrodes.

The method may conclude with an assay or test method used to identify the pathogens, such as immunoassay, array biosensors, PCR, rapid PCR, IFA, ELISA, ECL, culturing, mass spectrometry, and the like. Assaying denotes testing for or detecting the presence or quantity of a microorganism or a unique component thereof, and it includes detecting the presence of a microorganism in a specimen or to make a qualitative assessment thereof.

The various aspects of the invention summarized above are believed to have reduced process and apparatus/material costs, reduced time and labor requirements, reduced cold storage and logistical costs, and higher effectiveness than any previously known methods for concentrating and analyzing pathogenic microorganisms in food or water. Other features and advantages of the present invention will be apparent from the following more detailed description of preferred embodiments, taken in conjunction with the accompanying drawings which illustrate, by way of example, the principles of the invention.

DETAILED DESCRIPTION OF THE INVENTION

The present invention is directed to methods and systems for rapidly identifying biological agents such as bacteria, viruses, fungi and the like that may be present in an agricultural specimen. The methods of the present invention provide a process for rapidly and accurately identifying infectious biological agents and microorganisms.

Figures 1, 2:
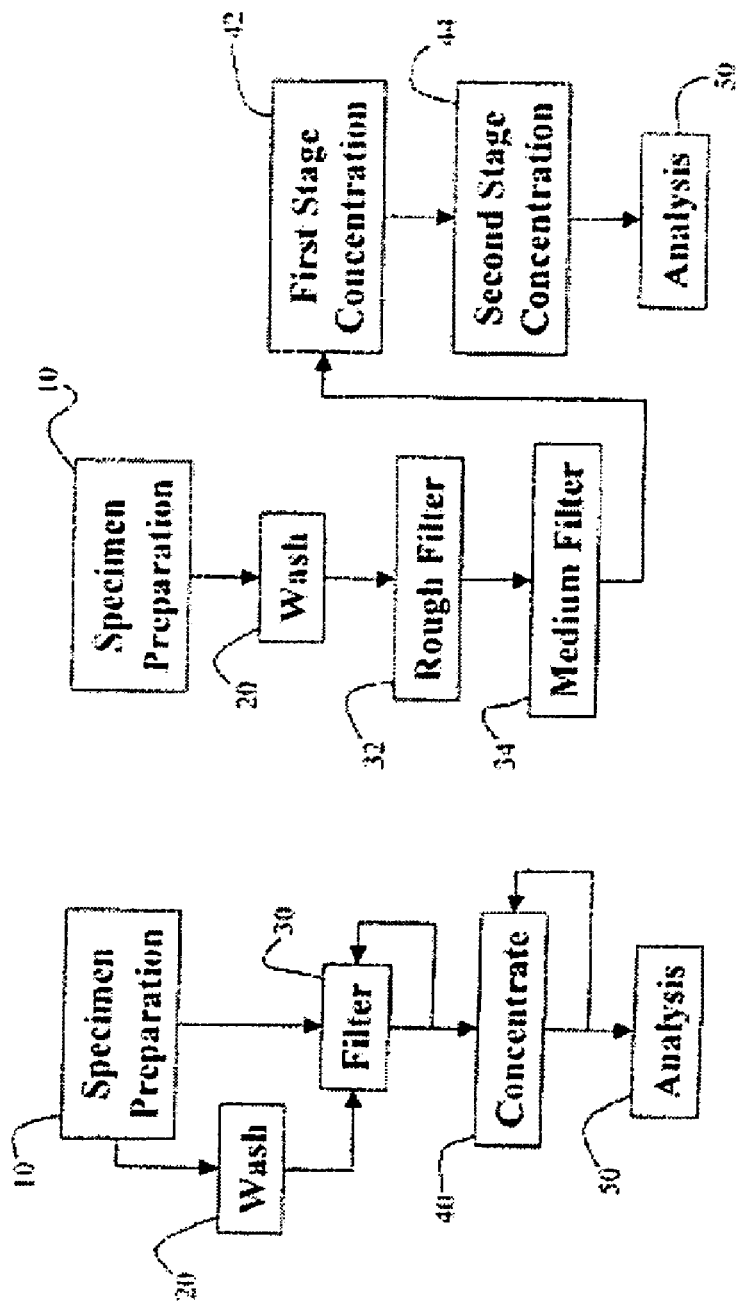
FIG. 1 is a flowchart illustrating a sequence of steps of an example method of the invention.
FIG. 2 is a flowchart illustrating a sequence of steps of another example method of the invention.

Referring to the Drawings, an example method of the invention is illustrated in FIG. 1. First, a specimen is prepared 10, which may include selecting a portion of a harvested crop and stomaching, grinding, macerating, or shredding it to produce an aqueous suspension, or alternatively a specimen may be washed 20 with an aqueous buffer or detergent solution, and the wash water collected as a specimen. The latter embodiment is particularly suited for continuous processing methods in which, e.g., vegetables are washed and then packaged, in which case the waste water or wash water may be continuously or periodically assayed for the presence of microorganisms. The washing step 20 may employ a vegetable washing machine that washes vegetables or fruit with phosphate buffered saline with Tween® thereby producing wash water, which is subsequently filtered 30, etc. For example, each wash produces 8 gallons and takes about 60-90 seconds. The vegetable washing machine may be started manually or after a prompt from a computer or automation system. The resulting liquid material is then filtered 30 to remove debris, particulate contaminates, and the like. The filtering step 30 may be repeated, each filtration may be the same or different, e.g., with filtration media having successively smaller pore sizes. Each filtration step 30 should be limited in order to limit the number of microorganisms that are discarded. Still referring to FIG. 1, the filtrate is then concentrated 40 in order to increase the number of microorganisms per unit volume. As illustrated, the method may include multiple concentration steps 40, each step being the same or different. Finally, the concentrated specimen is analyzed 50 for the presence of microorganisms.

In a similar manner, FIG. 2 illustrates another embodiment of the invention in which the wash water from a vegetable processing assembly line is analyzed, the method comprising two sequential filtration steps 32, 34 (in which filters of different pore sizes are used in order to remove progressively smaller particulate matter) and two different concentration steps 42, 44 in sequence. For example, after vegetables are washed, the wash water may be rough filtered 32 (about 50-250 microns, depending on the sediment profile). After rough filtering 32 a medium filter 34 (e.g., 10 micron, which removes dirt and debris) may be used prior to the first water concentration stage 42. A first stage concentration step 42 may employ hollow fiber or ceramic filtering technology with 25-50 nanometer pores (sufficient to capture/retain viruses and bacteria). This may include multiple parallel filters to reduce filtering time for the needed capacity. A second stage concentration step 44 concentrates (e.g., by magnetic beads, centrifuge, and nano-pore filtering) the specimen again down to a very small volume, which is suitable for further analysis. A two-step concentration process allows for large volumes (40-2000 L) to be concentrated down in a first stage 42 to about 250 mL to 20 L and then in the second stage 44 down to about 1 mL to 1 L.

Figure 3:
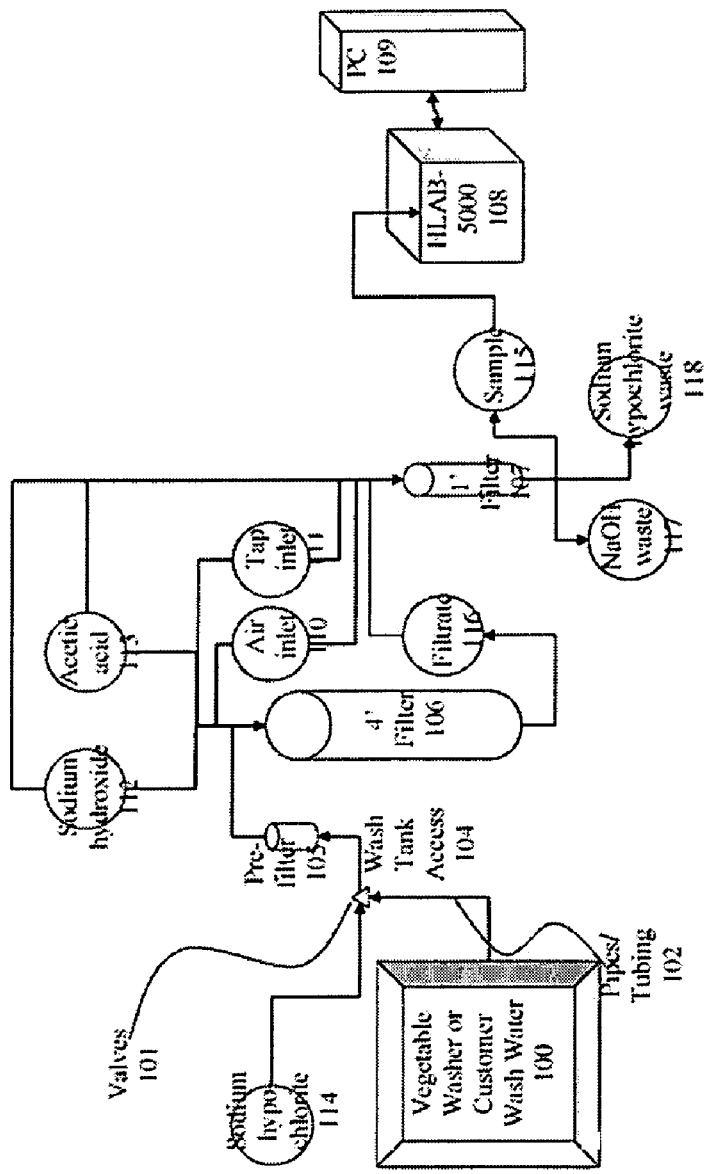
FIG. 3 is a schematic representation of some example components used in a method according to an embodiment of the invention.
Figure 4:
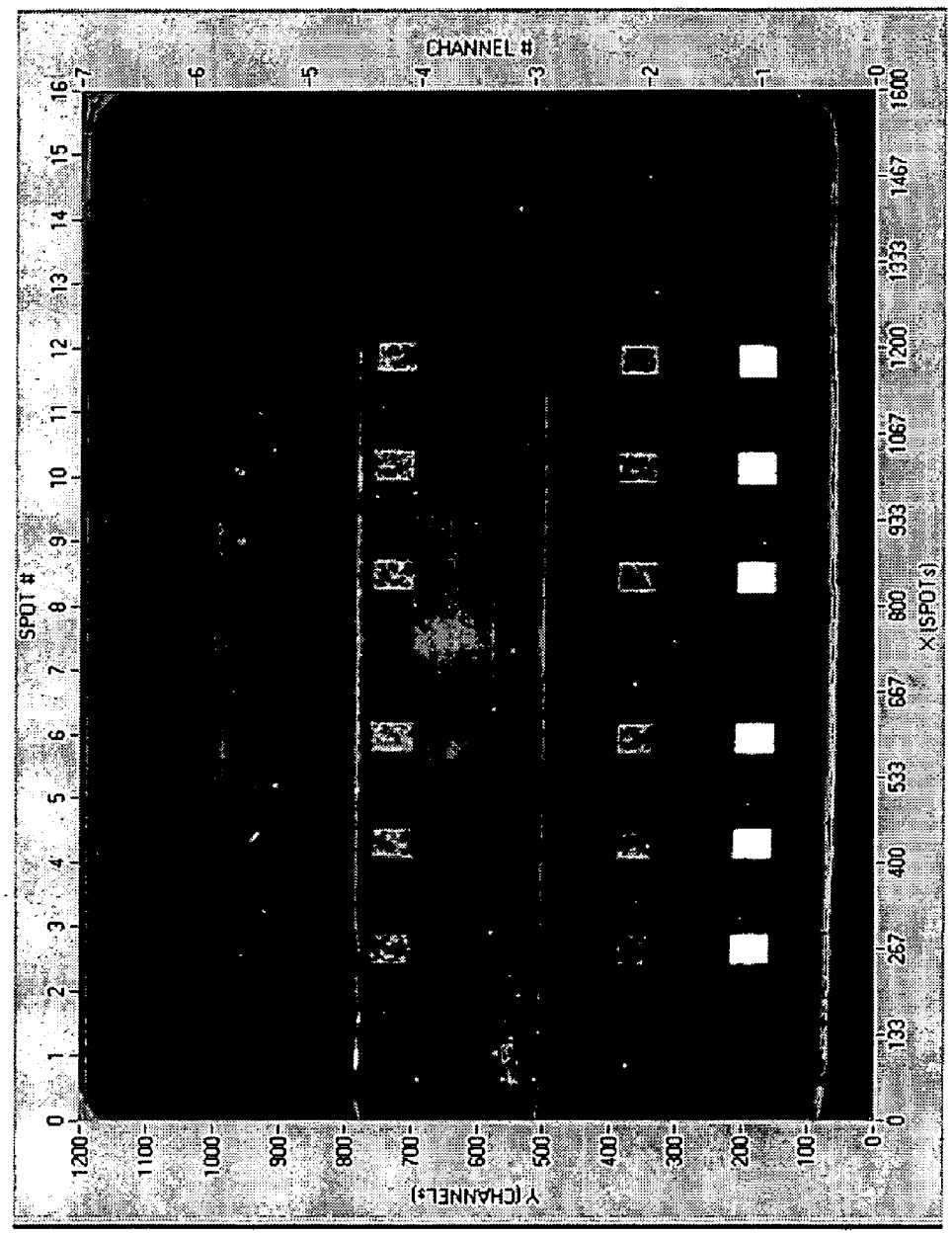
FIGS. 4 and 5 are images of an example *E. coli* detection in spinach according to an embodiment of the invention.
Figure 5:
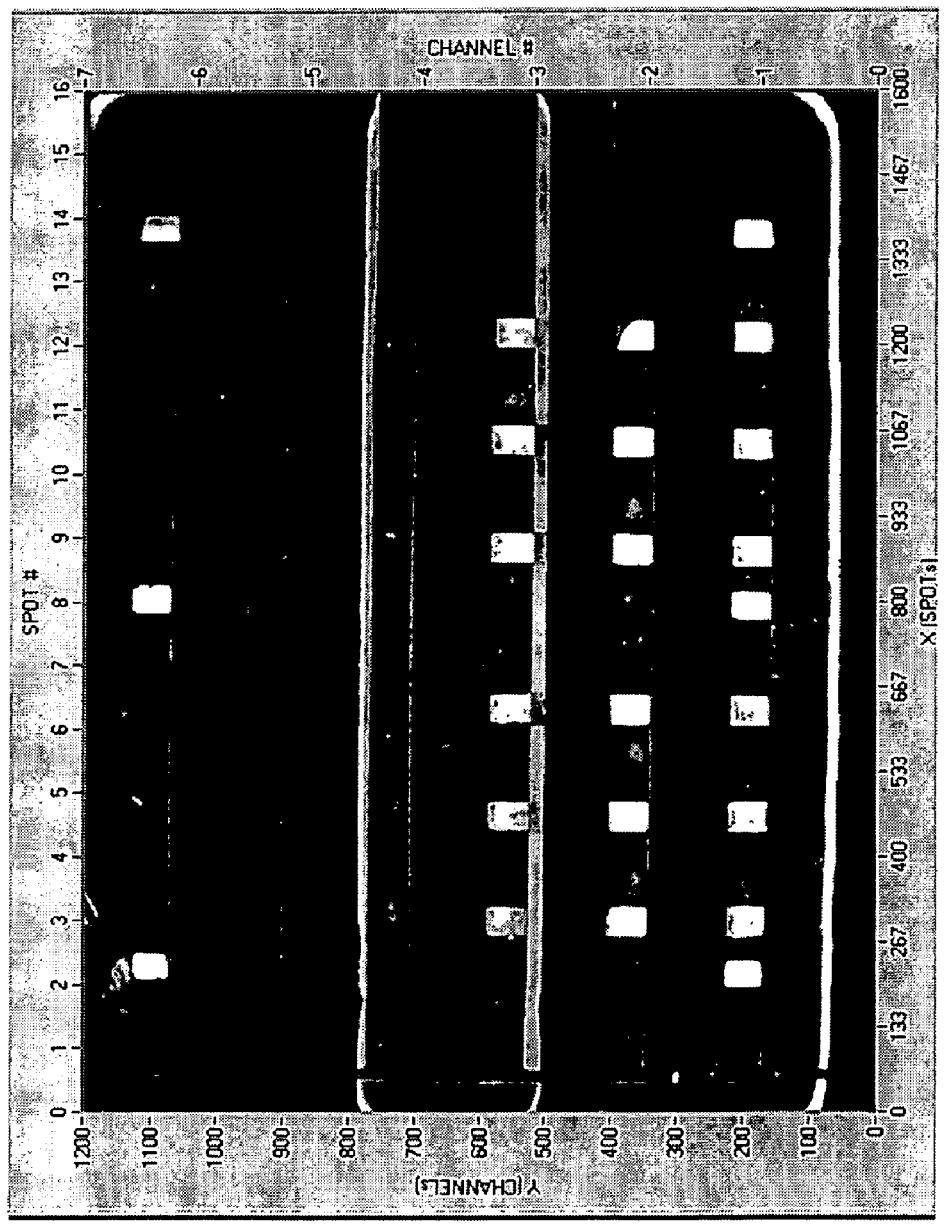

Referring to FIG. 3, some example components used in a method according to an embodiment of the invention include a vegetable washer (or wash water) 100, valves 101, tubing 102, pumps 103, a connection to access wash tank 104, a pre-filter 105, a large (4') ultrafilter 106, a small (1') ultrafilter 107, an optical waveguide detection system 108, a personal computer 109, an air inlet 110, a water (tap) inlet 111, a first cleaning solution tank 112 containing a sodium hydroxide solution with optional urea, a second cleaning solution tank 113 containing an acetic acid solution, a third cleaning solution tank 114 containing a sodium hypochlorite solution, a sample storage tank 115, a filtrate tank 116, a NaOH (sodium hydroxide) waste storage tank 117, and an optional NaOCl (sodium hypochlorite) waste storage tank 118. The valves 101, tubes 102, and pumps 103 form connections between the wash tank access fitting 104, the filters 105-107 and the air port 110. Steps of a method of concentrating and analyzing microorganisms in an agricultural specimen are implemented by the operation of the valves and pumps, which are controlled by a computer program running on a personal computer 109.

Still referring to FIG. 3, in an example method, wash water to be sampled is supplied from a vegetable wash tank 100 for processing. Once in the system, the wash water is pumped through a pre-filter 105 to pull out sediment and other unwanted materials. The pre-filtered water continues through valves 101 and tubing 102 to be pumped through a large ultrafilter 106. The entire designated sample is pumped through this filter 106. The filter 106 has ports to allow for reverse flow of liquid through the membrane, flushing of the filter core and gas (e.g., air, nitrogen) flow through the filter core to remove clogging material. Since the clogging material will also contain wanted sample, the flush is stored in a tank and is then pumped through the small ultrafilter 107. The small ultrafilter 107 has the same ports for flushing, except this filter 107 is only flushed once at the end of the wash water processing. The single, final flush is the concentrated sample that is then passed to the optical waveguide detection system 108 for analysis. The concentration portion of the filtration/concentration system signals to the optical waveguide detection system 108 that the sample is ready for assay and analysis. The detection system 108 begins the assay process as soon as it receives the signal from the concentrator. The detection system 108 automatically draws concentrated sample from the final flush container 115 and performs the assay.

When the assay is complete, the system is set up for an automated cleaning cycle of the entire system. There are many cleaning protocols, two of which are as follows: one cleaning protocol is for the filters 105-107 and another is for the tubing 102, valves 101 and pumps 103 outside of the filter-to-filter connection. The cleaning of the filters 105-107 is a two step process. Cleaning solution tanks 112-113 of NaOH/urea and acetic acid are introduced sequentially to the filters 105-107 through valve 101 and piping 102 connections. Each cleaning solution tank 112-113 has its own connections into the fluidic line leading to the filters 105-107. The remainder of the concentration system is cleaned and sanitized using a sodium hypochlorite solution stored in a separate cleaning solution tank 114. The sodium hypochlorite solution flows through all of the piping 102 that contacts a sample.

In the embodiment depicted in FIG. 3, the one-way directional valves 101 are controlled by the computer program, which is running on the personal computer 109. Through the computer program the user can open and close the valves 101. The tubing/piping 102 connects the valves 101, pumps 103, tanks 112-118 and filters 105-107 to allow the wash water to flow through the system. Diaphragm pumps 103 move liquid by filling a chamber then expelling its contents. The fluid never comes into contact with the mechanical parts of the pump, only the fill chambers. The pumps 103 are turned on at system set-up, but their running is controlled by the valves 101 in the same line. The valves 101 maintain pressure in the system when they are closed and the pump 103 doesn't force liquid through the valves 101. When the valves 101 are open, liquid is free to move through the tubing/piping 102 and the pump 103 runs to move as much liquid as possible through the system. The connection to access wash tank 104 a simple threaded connector on the end of a piece of tubing coming from the filtration/concentration system that screws onto a matched connector on the vegetable washer 100.

The pre-filter 105 is a 5 or 10 micron filter that prevents debris having a size larger than the rated size of the filter. A 5 micron filter would stop material that is 5 microns or larger from passing through it and allow particles smaller than 5 microns to pass through. The large ultrafilter 106 is a hollow-fiber ultrafilter that stops particles 25 nanometers or larger from passing through it and allows particles smaller than 25 nanometers to pass through. The hollow-fiber filter works by pushing incoming sample up into the hollow fibers. The only way for fluid to exit the fibers is to pass through the fiber wall trapping particles of 25 nanometers or larger inside the fibers. The liquid that passes through the fiber wall then exits the fiber through an exit port and is discarded from the system as excess liquid volume. The hollow-fiber ultrafilter 106 according to this embodiment is approximately 4 feet (1.2 m) tall with a 4 inch (10 cm) diameter and has fibers with a 1.5 millimeter diameter due to its ability to handle more complex, heavily loaded samples.

The small ultrafilter 107 is a hollow-fiber ultrafilter that stops particles 25 nanometers or larger from passing through it and allows particles smaller than 25 nanometers to pass through. The hollow-fiber filter 107 works by pushing incoming sample up into the hollow fibers. The only way for fluid to exit the fibers is to pass through the fiber wall trapping particles of 25 nanometers or larger inside the fibers. The liquid that passes through the fiber wall then exits the fiber through an exit port and is discarded from the system as excess liquid volume. The hollow-fiber ultrafilter 107 of this embodiment is approximately 1 foot (30 cm) tall with a 1 inch (2.5 cm) diameter and has fibers with a 1.5 millimeter diameter due to its ability to handle more complex, heavily loaded samples.

Still referring to FIG. 3, the optical waveguide detection system 108 automatically draws in sample, assays it for the targets and analyzes the data. See, e.g., U.S. Pat. No. 6,192,168 (assigned to the United States Navy). The computer 109 controls and coordinates all of the other components of the system through a customized program. Using non-lubricated air and on-board air filtration, the air inlet 110 allows air to be used when flushing out the ultrafilters 106-107, which increases the recovered yield from the filters and the cleaning efficiency. The water (tap) inlet 111 allows for tap water to be delivered to the system for flushing and clearing of the system. It is used after sodium hydroxide/urea and acetic acid cleaning to remove excess reagent. The first cleaning solution tank 112 contains an aqueous sodium hydroxide (NaOH) solution, optionally containing urea, used to clean the ultrafilters 106-107. This solution restores filter function back to its original capability before running any sample through it. The second cleaning solution tank 113 contains an aqueous acetic acid solution that is used to neutralize any base (sodium hydroxide) left in the system after filter cleaning/regeneration. The third cleaning solution tank 114 contains an aqueous sodium hypochlorite (bleach) solution that is used to clean and sanitize the remaining piping/tubing 102, valves 101 and pumps 103 in the system. The sample storage tank 115 holds the concentrated sample for the detector 108 to draw from. The filtrate tank 116 stores process water after it has gone through the first (4') ultrafilter before it is processed through the second (1') filter. The NaOH waste storage tank 117 stores the NaOH solution after it has been run through the system, and the optional NaOCl waste storage tank 118 stores the sodium hypochlorite solution after it has been run through the system.

The invention is further illustrated by the following examples, which should not be construed as further limiting.

EXAMPLES

Test run of spinach. Using a large food specimen of >100 grams to >10 kg (e.g., 20 kg), with single or multiple sequential concentration steps (e.g., starting with 4 kg of spinach per batch, run 5 times, with a total of 20,000 *E. coli*) followed by an assay tests results in pathogen data without culturing. This significantly shortens the time between specimen collection and test result from days to hours. An example method is carried out as follows: Provide 5 batches (4 kg each) of spinach. Place 200,00 *E. coli* (2 mL of $1\times10^4$ O157:H7 *E. coli*) on the leaves in the first of the 5 batches, letting them dry on the leaves before processing. Run the 4 kg batch of leaves through the vegetable washing machine with the 8 gallon 90 second spray wash. After the washing machine, run the vegetable wash through the 50 micron filter, 10 micron filter, and the automated filtration unit, until all 8 gallons have been processed. Recover the concentrated sample in approximately 250 mL. Repeat the preceding steps for the other four batches to produce approximately 1.25 L of concentrate. Perform the magnetic bead or fluid concentration on 1.25 L, generating a small volume concentrate (1-3 mL). Run the final concentrate from this through an array biosensor and analyze it.

Fresh spinach leaves. $10^5$ cfu heat-killed *E. coli* O157:H7, combined with approximately 80 oz. (2.3 kg) fresh spinach leaves and 8 gallons (30 L) of distilled water, was processed through the system depicted in FIG. 3. This included a final pathogen collection stage using an X-Flow® filter (available from Norit N. V., Zenderen, The Netherlands; X-FLOW® is a registered trademark of X-Flow B. V., Enschede, The Netherlands).

After the total volume was processed, the pathogens were retrieved from the X-Flow® filter in four individual samples, using three different sample collection techniques. (1) The first 250 mL of sample was collected using a backflush, a method that reverses the flow of the permeate. Distilled water entered on the permeate side of the filter, forcing sample to exit through the filter core. (2) A purge was used to collect the second 250 mL sample. Distilled water was run directly through the core of the filter. (3) A sample collection technique using pressurized gas was then introduced. The filter core was purged of liquid using the pressurized gas. Once the core was empty, the gas continued to purge the filter while a backflush (as described in 1) was performed. After a predetermined volume of water passed through the permeate side of the filter, the backflush was stopped. The pressurized gas continued to purge until all remaining liquid sample was cleared from the filter core. Again, 250 mL of sample was collected. (4) The final 250 mL sample was obtained by repeating the purge process (as described in 2).

The four samples were each concentrated down to approximately 1-2 mL using a centrifuge before being processed through an optical waveguide detection device. Each was processed as an individual sample for *E. coli* O157:H7 detection. *E. coli* O157:H7 was detected in each of the four samples, as depicted in FIG. 4 (in which channels 1 and 6 are negative and positive control samples). However, the degree of detection varied depending on the sample collection method used. The purge technique (channel 5, FIG. 4) was least effective method of obtaining the *E. coli* O157:H7. The highest levels of detection occurred in the backflush and pressurized gas with reverse permeate flow samples (channels 2 and 4). Although the pressurized gas with reverse permeate flow was the third sample collected, the intensities (amount of detection, the "brightness" of the spots in FIG. 4) were equal to that of the backflush sample (channel 2), indicating that the backflush alone was not effective at removing the majority of the pathogens from the filter.

*E. coli* in water. Four 100 mL samples of known amounts of *E. coli* O157:H7 were prepared in distilled water. The samples included $10^4$-$10^7$ cfu *E. coli* O157:H7. For the positive control, a 1 mL sample of 105 cfu/mL *E. coli* O157:H7 was used. All 100 mL of each sample were exposed to the biochip at a rate of 1.5 mL/min using a forward motion. The positive control was also processed using the same rate. After the sample portion of the assay, anti-*E. coli* tracers were passed over the slide surface, followed by a final wash before imaging and data analysis. Cy5 chicken antibodies were also used as positive controls in 2 of the 6 channels (FIG. 5, channels 1 and 6).

*E. coli* O157:H7 was detected in each of the four samples (in FIG. 5, channel 2 is $10^7$ cfu/100 mL *E. coli*, channel 3 is $10^6$ cfu/100 mL, channel 4 is $10^5$ cfu/100 mL, and channel 5 is $10^4$ cfu/100 mL). In previous experiments where only 800 L were used for each sample, the lowest concentration of *E. coli* O157:H7 successfully detected was $10^4$ cfu/mL. For this experiment, the large volume samples ranged in concentration from $10^2$-$10^5$ cfu/mL. Using small volumes, the lower concentration levels would likely have been poorly detectable. However, in this larger sample size, more sample was exposed to the biochip in the assay portion of the system effectively further concentrating the pathogens, allowing for positive detection of *E. coli* O157:H7 with a detection limit of $10^4$ cfu/mL or lower.

While the invention has been described with reference to preferred embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to any particular embodiment disclosed as the best mode contemplated for carrying out this invention, but that the invention will include all embodiments falling within the scope of the appended claims.

The invention claimed is:

1. A method of concentrating and analyzing microorganisms in an agricultural specimen potentially contaminated by such microorganisms comprising the steps of
   collecting an agricultural specimen comprising a quantity of vegetation that is suspected of containing microorganisms, wherein
      said quantity is a statistically significant sample of a harvested crop;
   filtering said agricultural specimen to thereby produce a filtered specimen, wherein
      said filtering step preferentially removes interfering materials that are not microorganisms;
   concentrating said filtered specimen to thereby produce a concentrated specimen, wherein
      said concentrating step enriches the quantity of microorganisms in said specimen by at least ten-fold; and thereafter
   analyzing said concentrated specimen for the presence or quantity of said microorganisms.

2. The method of claim 1, wherein said specimen is aqueous.

3. The method of claim 1, wherein said specimen is a waste or wash liquid from a water-based vegetation washing process.

4. The method of claim 1, wherein said specimen comprises an aqueous suspension of macerated or ground vegetation in water.

5. The method of claim 1, wherein said quantity of vegetation is at least one kilogram of vegetation per hectare of harvested crop.

6. The method of claim 1, wherein said quantity of vegetation is at least one kilogram.

7. The method of claim 1, wherein said quantity of vegetation is at least twenty kilograms.

8. The method of claim 1, wherein said harvested crop is selected from the group consisting of sugar cane, maize, wheat, rice, potatoes, sugar beet, soybean, barley, tomato, spinach, lettuce, broccoli, cauliflower, beans, fruits, nuts, tobacco, mushrooms, alfalfa, oats, millet, rye, sorghum, canola, cottonseed, flaxseed, mustard seed, peanuts, rapeseed, safflower, sunflower, cotton, lentils, peas, coffee, hops, sweet potatoes, and taro.

9. The method of claim 1, wherein the concentration of microorganisms in said concentrated specimen is at least 1000-fold greater than the concentration of microorganisms in said agricultural specimen.

10. The method of claim 1, wherein said microorganisms are associated with an animal or human disease.

11. The method of claim 1, wherein said microorganisms comprise one or more microorganisms selected from the group of microorganisms as set forth in the Appendix attached hereto.

12. The method of claim 1, wherein said microorganisms are intact, lysed, ground or otherwise fragmented.

13. The method of claim 1, wherein said concentrating step is selected from the group consisting of nano-pore filtering, ultrafiltration, magnetic bead concentration, centrifugation, tangential filtering, hollow fiber concentration, ceramic filtering, membrane module filtering, and electric field concentration.

14. The method of claim 1, wherein said method comprises two or more concentrating steps, which may be the same or different.

15. The method of claim 1, wherein said method comprises two or more concentrating steps, which may be the same or different.

16. The method of claim 1, wherein said method is essentially free of a culturing step.

17. A method of concentrating and analyzing microorganisms in an agricultural specimen potentially contaminated by such microorganisms comprising the steps of
   collecting an agricultural specimen comprising a quantity of vegetation that is suspected of containing a microorganism, wherein
      said quantity is at least one kilogram of a crop per harvested hectare;
   washing said agricultural specimen with an aqueous solution comprising a detergent to thereby produce a wash specimen;
   filtering said wash specimen to thereby produce a filtered specimen, wherein
      said filtering step preferentially removes interfering materials that are not microorganisms, and
      said filtering step comprises
         passing said wash specimen through a first filter, and thereafter
         passing said wash specimen through a second filter, wherein the pore size of said first filter is larger than the pore size of said second filter, and the pore size of said second filter is larger than the average size of said microorganism;
   concentrating said filtered specimen to thereby produce a concentrated specimen, wherein
      said concentrating step enriches the quantity of microorganisms in said specimen by at least ten-fold; and thereafter
   analyzing said concentrated specimen for the presence or quantity of said microorganisms.

* * * * *